United States Patent
Hornsteiner

(10) Patent No.: US 11,369,283 B2
(45) Date of Patent: Jun. 28, 2022

(54) IMPLANT MAGNET DISTANCE DETERMINATION

(71) Applicant: MED-EL Elektromedizinische Geraete GmbH, Innsbruck (AT)

(72) Inventor: Christoph Hornsteiner, Mittenwald (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1131 days.

(21) Appl. No.: 14/522,677

(22) Filed: Oct. 24, 2014

(65) Prior Publication Data

US 2015/0119687 A1  Apr. 30, 2015

Related U.S. Application Data

(60) Provisional application No. 61/895,070, filed on Oct. 24, 2013.

(51) Int. Cl.
*A61B 5/06* (2006.01)
*A61B 5/05* (2021.01)
(Continued)

(52) U.S. Cl.
CPC ............. *A61B 5/062* (2013.01); *A61B 5/05* (2013.01); *A61B 5/1075* (2013.01);
(Continued)

(58) Field of Classification Search
CPC combination set(s) only.
See application file for complete search history.

(56) References Cited

U.S. PATENT DOCUMENTS 6,138,681 A * 10/2000 Chen ................. A61B 5/06
128/897
6,366,817 B1 * 4/2002 Kung ................. A61N 1/3787
607/61
(Continued)

FOREIGN PATENT DOCUMENTS

GB   2453199 A  *  4/2009  ....... E21B 47/02224

OTHER PUBLICATIONS

Archive.org capture of Data Presentation: Bar Graphs by Barcelona Field Studies Centre pub. online on Jan. 21, 2012 at <http://web.archive.org/web/20120121010123/https://geographyfieldwork.com/DataPresentationBarCharts.htm> accessed Apr. 13, 2020 (Year: 2012).*

(Continued)

*Primary Examiner* — Katherine L Fernandez
*Assistant Examiner* — Michael S Kellogg
(74) *Attorney, Agent, or Firm* — Sunstein LLP

(57) ABSTRACT

A method is described for estimating skin thickness over an implanted magnet. A plane is defined that is perpendicular to the skin of a patient over an implanted magnet and characterized by x- and y-axis coordinates. The magnetic field strength of the implanted magnet is measured using an array of magnetic sensors on the skin of the patient. From the measured magnetic field strength, at least one x-axis coordinate in the plane is determined for at least one y-axis zero position on the array where a y-axis component of the measured magnetic field strength is zero. From that, a y-axis coordinate of the at least one y-axis zero is calculated as a function of the at least one x-axis coordinate, such that the y-axis coordinate represents thickness of the skin over the implanted magnet.

14 Claims, 13 Drawing Sheets
(8 of 13 Drawing Sheet(s) Filed in Color)

(51) Int. Cl.
*A61B 5/107* (2006.01)
*A61B 5/00* (2006.01)
*G01B 7/06* (2006.01)
*G01R 33/00* (2006.01)
*G01B 7/14* (2006.01)

(52) U.S. Cl.
CPC .............. *A61B 5/7278* (2013.01); *G01B 7/10* (2013.01); *G01R 33/0094* (2013.01); *A61B 2562/0223* (2013.01); *A61B 2562/046* (2013.01); *G01B 7/14* (2013.01)

(56) References Cited

U.S. PATENT DOCUMENTS

| | | | |
|---|---|---|---|
| 7,615,993 B2 | 11/2009 | Takahashi | |
| 7,772,950 B2 | 8/2010 | Tunay | |
| 7,952,357 B2* | 5/2011 | Cole | E21B 47/02224 175/45 |
| 8,452,412 B2* | 5/2013 | Ibrahim | A61B 5/4872 607/31 |
| 8,701,677 B2* | 4/2014 | Duan | A61B 1/00158 128/898 |
| 2004/0130316 A1* | 7/2004 | Grueger | G01D 5/145 324/207.2 |
| 2005/0075562 A1* | 4/2005 | Szakelyhidi | A61B 5/06 600/424 |
| 2007/0163367 A1* | 7/2007 | Sherman | G01R 33/0206 73/866 |
| 2009/0030485 A1 | 1/2009 | Mishra et al. | |
| 2009/0108838 A1* | 4/2009 | Moser | G01N 27/90 324/240 |
| 2011/0031961 A1* | 2/2011 | Durand | A61B 1/267 324/207.2 |
| 2011/0264172 A1 | 10/2011 | Zimmerling et al. | |
| 2011/0301913 A1* | 12/2011 | Matsumoto | G01D 5/145 702/151 |
| 2012/0302869 A1* | 11/2012 | Koyrakh | A61B 5/062 600/409 |

OTHER PUBLICATIONS

International Searching Authority, Authorized Officer Shane Thomas, International Search Report and Written Opinion—PCT/US14/62082, dated Jan. 14, 2015, 11 pages.

* cited by examiner

IMPLANT MAGNET DISTANCE DETERMINATION

This application claims priority from U.S. Provisional Patent Application 61/895,070, filed Oct. 24, 2014, which is incorporated herein by reference in its entirety.

FIELD OF THE INVENTION

The present invention relates to implantable medical devices, and specifically, to estimating the location of magnetic elements in such devices.

BACKGROUND ART

Some implantable medical systems such as Middle Ear Implants (MEI's) and Cochlear Implants (CI's) employ attachment magnets in the implantable part and an external part to hold the external part magnetically in place over the implant. For example, as shown in FIG. 1, a typical cochlear implant system may include an external transmitter housing 101 containing transmitting coils 102 and an external attachment magnet 103. The external attachment magnet 103 has a conventional disk-shape and a north-south magnetic dipole having an axis that is perpendicular to the skin of the patient to produce external magnetic field lines 104 as shown. Implanted under the patient's skin is a corresponding receiver assembly 105 having similar receiving coils 106 and an implant magnet 107. The implant magnet 107 also has a disk-shape and a north-south magnetic dipole having a magnetic axis that is perpendicular to the skin of the patient to produce internal magnetic field lines 108 as shown. The internal receiver housing 105 is surgically implanted and fixed in place within the patient's body. The external transmitter housing 101 is placed in proper position over the skin covering the internal receiver assembly 105 and held in place by interaction between the internal magnetic field lines 108 and the external magnetic field lines 104. Rf signals from the transmitter coils 102 couple data and/or power to the receiving coil 106 which is in communication with an implanted processor module (not shown).

After implantation of such devices, sometimes problems can arise such as inadequate magnetic holding force of the external part. In such circumstances, the exact distance from the skin surface to the implant magnet is generally unknown, so it would not be clear if the problem is because the distance is too great or the implant magnet has partially lost magnetization. During implantation, the surgeon can physically measure the skin thickness over the implant, but that is not possible after the surgery. An absolute magnetic field measurement may be possible if the magnetization strength is known, but that may not generally be the case.

U.S. Pat. No. 7,561,051 describes a device that is able to determine the location of an implanted magnet by a passive measurement of the magnetic field. The device uses magnetic sensors in an array that can measure the direction of the magnetic field and the magnetic field strength. The distance calculation used is complicated and computationally demanding, making this approach less useful for battery operated devices.

SUMMARY OF THE INVENTION

Embodiments of the present invention are directed to a method for estimating skin thickness over an implanted magnet. A plane is defined that is perpendicular to the skin of a patient over an implanted magnet and characterized by x- and y-axis coordinates. The magnetic field strength of the implanted magnet is measured using an array of magnetic sensors on the skin of the patient. From the measured magnetic field strength, at least one x-axis coordinate in the plane is determined for at least one y-axis zero position on the array where a y-axis component of the measured magnetic field strength is zero. From that, a y-axis coordinate of the at least one y-axis zero is calculated as a function of the at least one x-axis coordinate, such that the y-axis coordinate represents thickness of the skin over the implanted magnet.

In further specific embodiments, the x-axis coordinates may be determined for two y-axis zero positions. The magnetic field strength may be measured using a one-dimensional or two-dimensional sensor array. Before taking the magnetic field strength measurements, the sensor array may be aligned by user interaction or without user interaction. Calculating the y-axis coordinate may further be a function of magnetic dipole moment rotation angle, and may be based on an iterative calculation process, or on a single step non-iterative calculation process. Calculating the y-axis coordinate also may be based on a trigonometric or non-trigonometric calculation process.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF SPECIFIC EMBODIMENTS

In general, the absolute magnetic field strength is not known after surgery so cannot be used as the basis for measuring distance to the implant magnet (skin thickness over the magnet). But the magnetic field lines as such are independent of the magnetization strength. Therefore a distance estimate can be made based on the field direction, which would need measurements of the magnetic field strength at different positions. The lowest distance for measurements is the plane of the skin surface.

Figure 1:
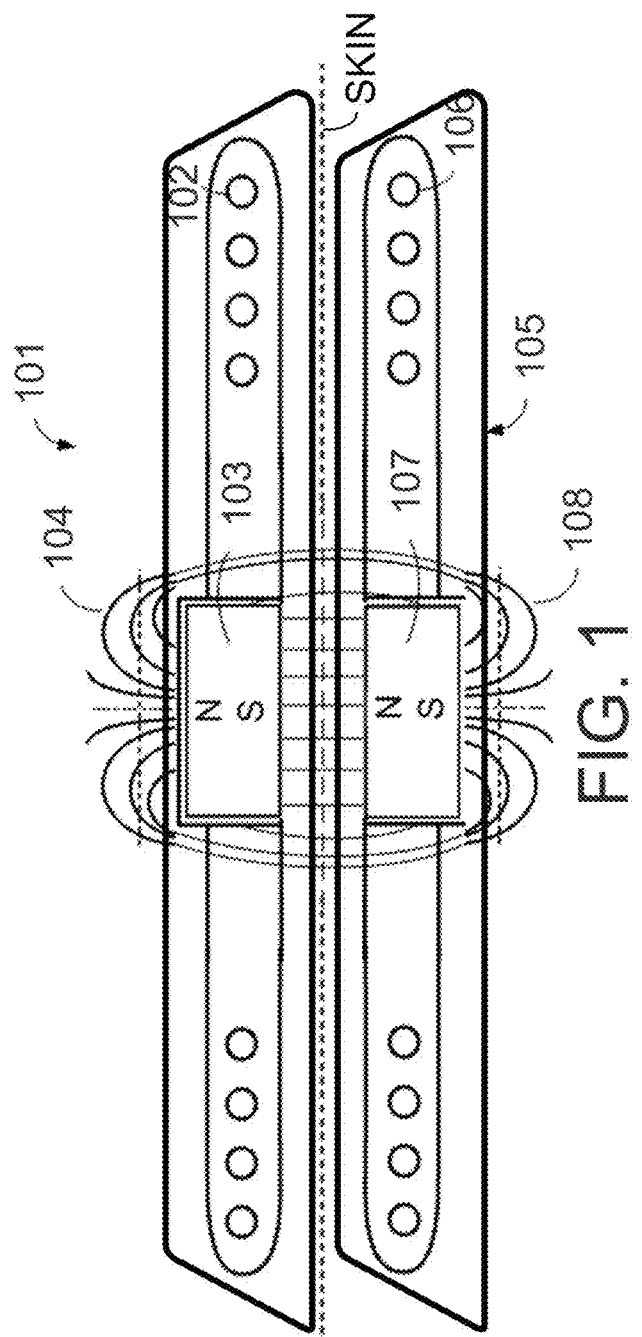
FIG. 1 shows portions of a typical cochlear implant system.
Figure 2:
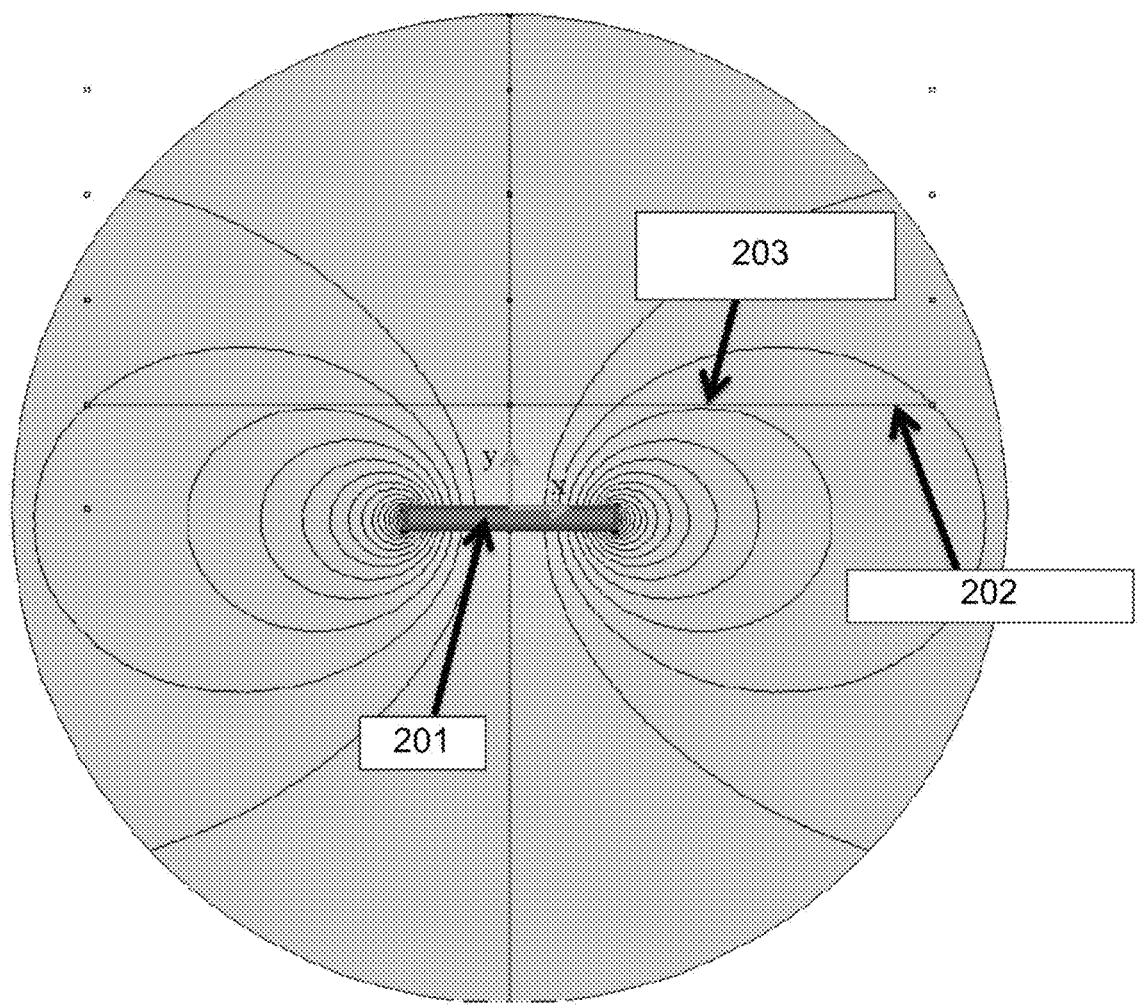
FIG. 2 shows an axis-symmetric simulation with magnetic field lines for an axially magnetized implant magnet.
Figure 3:
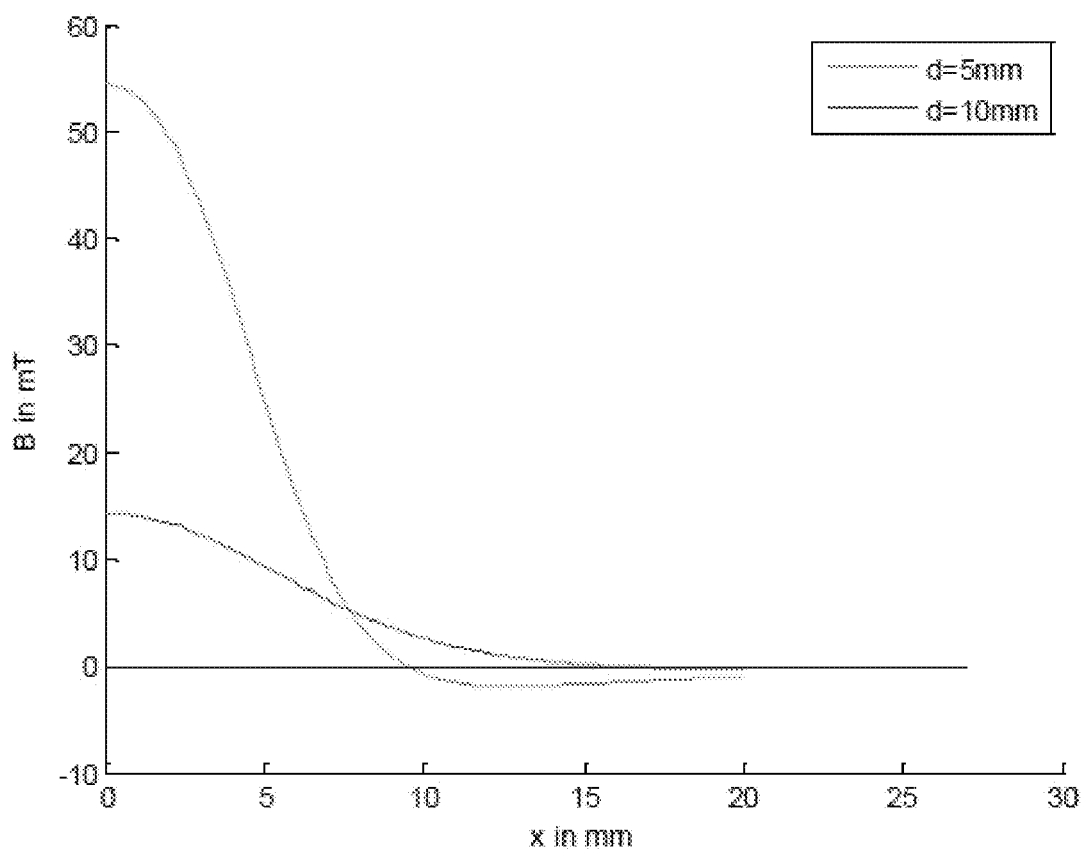
FIG. 3 shows a graph of the corresponding normal component of the magnetic field measured in FIG. 2.

FIG. 2 is an axis-symmetric simulation showing the magnetic field lines of an axial magnetized implant magnet 201, evaluating the normal field component along a field evaluation line 202 parallel to the implant magnet 201 (y is held constant). FIG. 3 shows a graph of the corresponding normal component of the magnetic field along the axis for the given field evaluation line 202. Since the absolute strength of the magnetic field is not needed, the field evaluation values are normalized to the value at x-axis zero position. At some point for each pole, there will be a zero y-component point 203 ($B_y$=0). In FIG. 3, the y-component will be zero at the zero crossing of the field evaluation lines on the y-axis. By determining the x-axis coordinate for the zero y-component point 203, it is then possible to calculate the y-coordinate at that point.

Explaining more fully and rigorously, the magnetic moment m of a magnetic field can be characterized by a vector potential:

$$A(r) = \frac{\mu_0}{4\pi} \frac{m \times r}{r^3}$$

and the field of a magnetic dipole moment can be represented in terms of a magnetic flux density B(r):

$$B(r) = \nabla \times A = \frac{\mu_0}{4\pi}\left(\frac{3r(m \cdot r)}{r^5} - \frac{m}{r^3}\right)$$

The dipole moment is oriented in y-direction and positioned at the origin of a Cartesian coordinate system:

$$m = m \begin{pmatrix} 0 \\ 1 \\ 0 \end{pmatrix}$$

The orientation of the magnetic dipole in this case is defined to be perpendicular to the patient skin. And an observing point is then located at:

$$r = \begin{pmatrix} x \\ y \\ z \end{pmatrix}, r = \sqrt{x^2 + y^2 + z^2}$$

Given the foregoing, the magnetic field can be represented as:

$$B(r) = \frac{\mu_0}{4\pi}\left(\frac{3rym}{r^5} - \frac{m}{r^3}\right)$$

and in the x-y plane (with z=0) following:

$$r = \sqrt{x^2 + y^2}$$

$$B_x(x, y) = \frac{\mu_0 m}{4\pi}\left(\frac{3xy}{r^5}\right) = \frac{\mu_0 m}{4\pi} \frac{3xy}{(x^2+y^2)^{\frac{5}{2}}}$$

-continued $$B_y(x, y) = \frac{\mu_0 m}{4\pi}\left(\frac{3y^2}{r^5} - \frac{1}{r^3}\right) = \frac{\mu_0 m}{4\pi} \frac{2y^2 - x^2}{(x^2+y^2)^{\frac{5}{2}}}$$

$$B_z(x, y) = 0$$

The zeros of the x-component $B_x(x,y)$=0 are located at x=0 and y=0. The zeros of the y-component $B_y(x,y)$=0 then are $2y^2-x^2=0 \Rightarrow x=\sqrt{2}y$. Therefore a measured zero x-position $x_0$ of the y-component $B_y(x_0,y_0)$=0 can be used to estimate the unknown y-position $$\hat{y}_0 = \frac{x_0}{\sqrt{2}}.$$

Figure 5A:
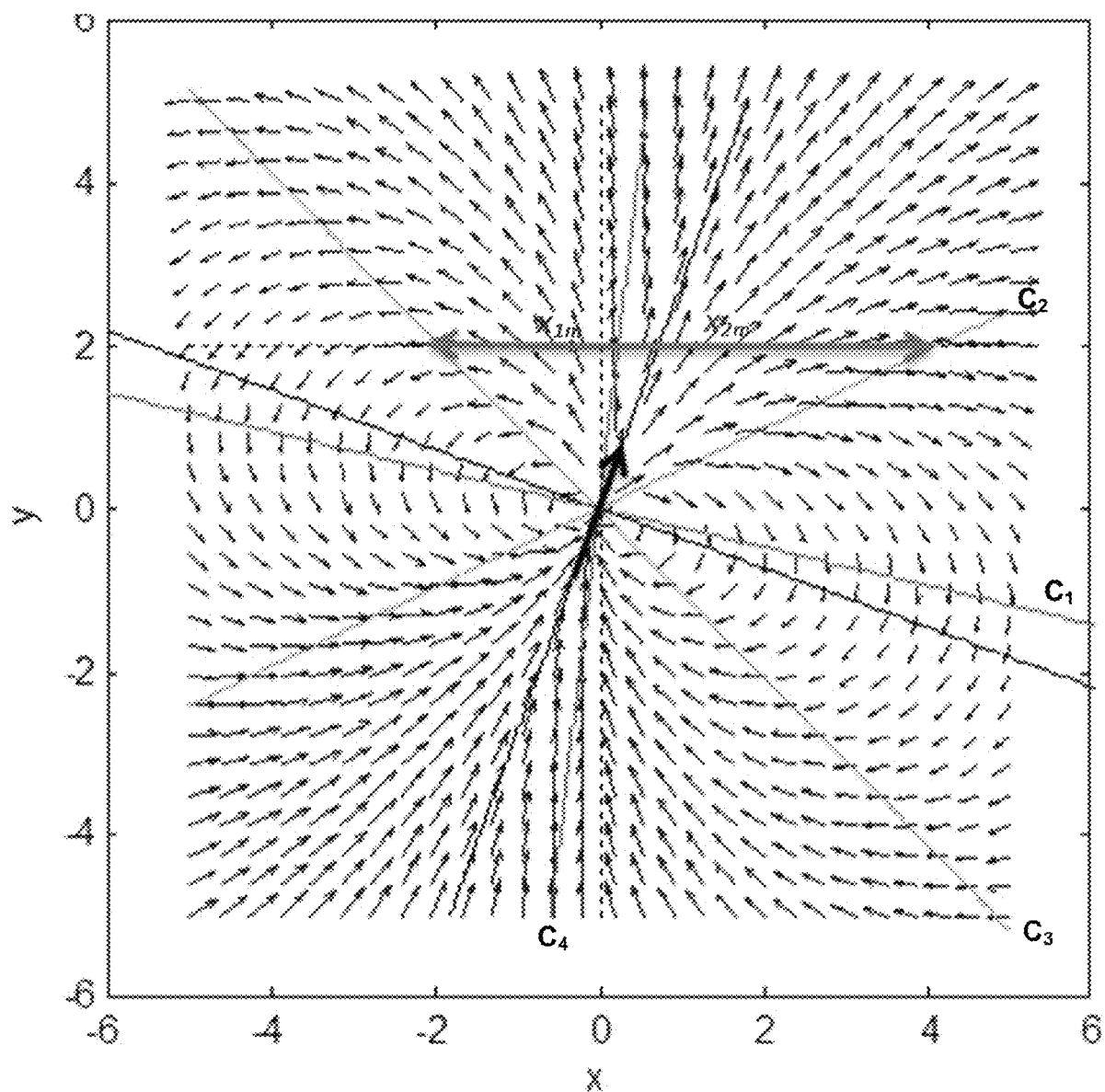
FIG. 5 A-B shows an example of the magnetic field vector lines for a given magnetic dipole moment vector having a rotation angle of 20°.

FIG. 5A snows an example of the magnetic field vector lines (the small arrows) for a given magnetic dipole moment vector (the large dark arrow in the center). The solid narrow lines crossing in the center indicate the positions where $B_y$=0 and the arrows $x_{1m}$ and $x_{2m}$ give the orientation of the magnetic sensing array.

Considering the more realistic case where there is some rotation of the dipole moment, again using the x-y plane (z=0), the magnetic dipole moment m is:

$$m = m \begin{pmatrix} \sin \alpha \\ \cos \alpha \\ 0 \end{pmatrix}$$

with a rotation angle $\alpha$. The magnetic field B is now characterized by x- and y-components:

$$B_x = \frac{2\sin(\alpha)x^2 + 3xy\cos(\alpha) - \sin(\alpha)y^2}{(x^2+y^2)^{5/2}}$$

$$B_y = \frac{-3xy\sin(\alpha) - 2\cos(\alpha)y^2 + \cos(\alpha)x^2}{(x^2+y^2)^{5/2}}$$

Then solving for a with $B_y$=0 yields:

$$\alpha = \arctan\left(1/3\frac{-2y^2+x^2}{xy}\right)$$

Now the magnetic field is measured at two x-positions $x_1$ and $x_2$ and assuming the same y in the chosen coordinate system:

$$\frac{-\left(\frac{2}{3}\right)y^2 + \left(\frac{1}{3}\right)x_1^2}{x_1 y} - \frac{-\left(\frac{2}{3}\right)y^2 + \left(\frac{1}{3}\right)x_2^2}{x_2 y} = 0 \overset{yields}{\to} \hat{y} = \sqrt{\frac{|x_1 x_2|}{2}}$$

The result is related to the geometric mean of both numbers and simplifies to the already shown result for $x_1$=$x_2$. It should be noted that now the points of x=0 (black dashed vertical) are different from the point of $B_x$=0 ($c_1$ and $c_4$) and also different from the moment axis (black arrow).

Figure 4:
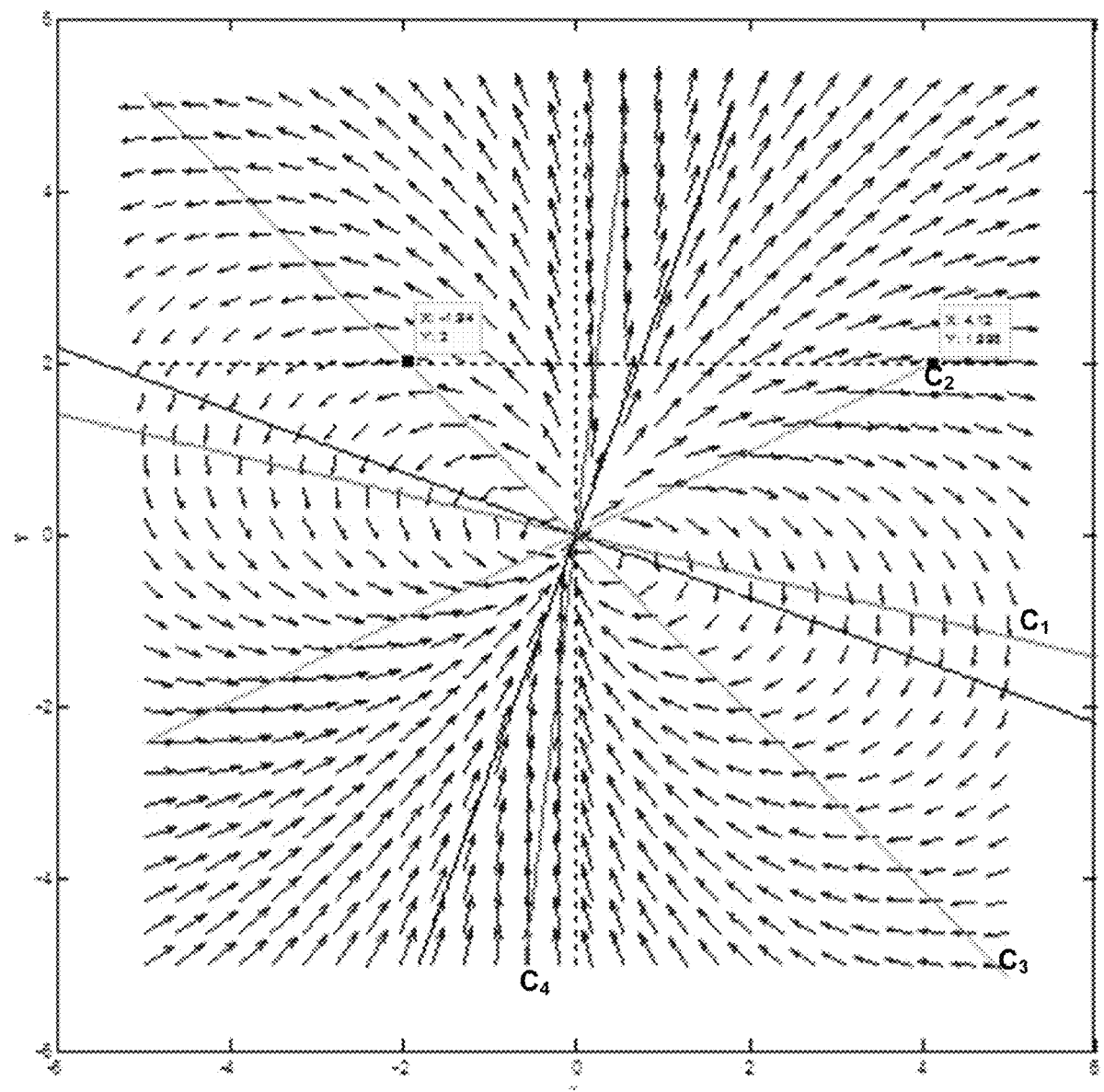
FIG. 4 shows an example of the magnetic field vector lines for a given magnetic dipole moment vector.

From the foregoing, FIG. 4 shows a specific example where $\alpha$=20° and y=2, which gives:

$$\hat{y} = \sqrt{\frac{|1.94 \cdot 4.12|}{2}} = 1.999$$

Putting all the foregoing into a specific efficient algorithm for finding the skin thickness in terms of the y-coordinate, the distance $x_{1m}$ is from left point $B_y=0$ to point $B_x=0$, and the distance $x_{2m}$ is from right point $B_y=0$ to point $B_x=0$. Then calculate a first estimate for distance y:

$$\hat{y} = \sqrt{\frac{|x_{1m}x_{2m}|}{2}}$$

Calculate an estimate for rotation angle:

$$\hat{\alpha} = \arctan\left(\frac{x_{2m}^2 - 2\hat{y}^2}{3x_{2m}\hat{y}}\right)$$

Then calculate an estimate for displacement of point $B_x=0$ to x=0

$$\widehat{x_3} = \frac{-3 + \sqrt{9 + 8(\tan \hat{\alpha})^2}}{4 \tan \hat{\alpha}} \hat{y}$$

And then update the measured distances:

$$x_2 = x_{1m} - \widehat{x_3}$$

$$x_2 = x_{2m} + \widehat{x_3}$$

from which:

$$\hat{y}' = \sqrt{\frac{|x_1 x_2|}{2}}$$

Which represents a better estimate for the unknown distance y'. The algorithm can be iterated to reduce the result error.

The first three calculations can be rolled into a single step without a trigonometric function:

$$\widehat{x_3} = -1/8 \frac{x_{1m}x_{2m}\left(-9 + \sqrt{\frac{49x_{1m}x_{2m} + 16x_{1m}^2 + 16x_{2m}^2}{x_{1m}x_{2m}}}\right)}{x_{1m} - x_{2m}}$$

Figure 6:
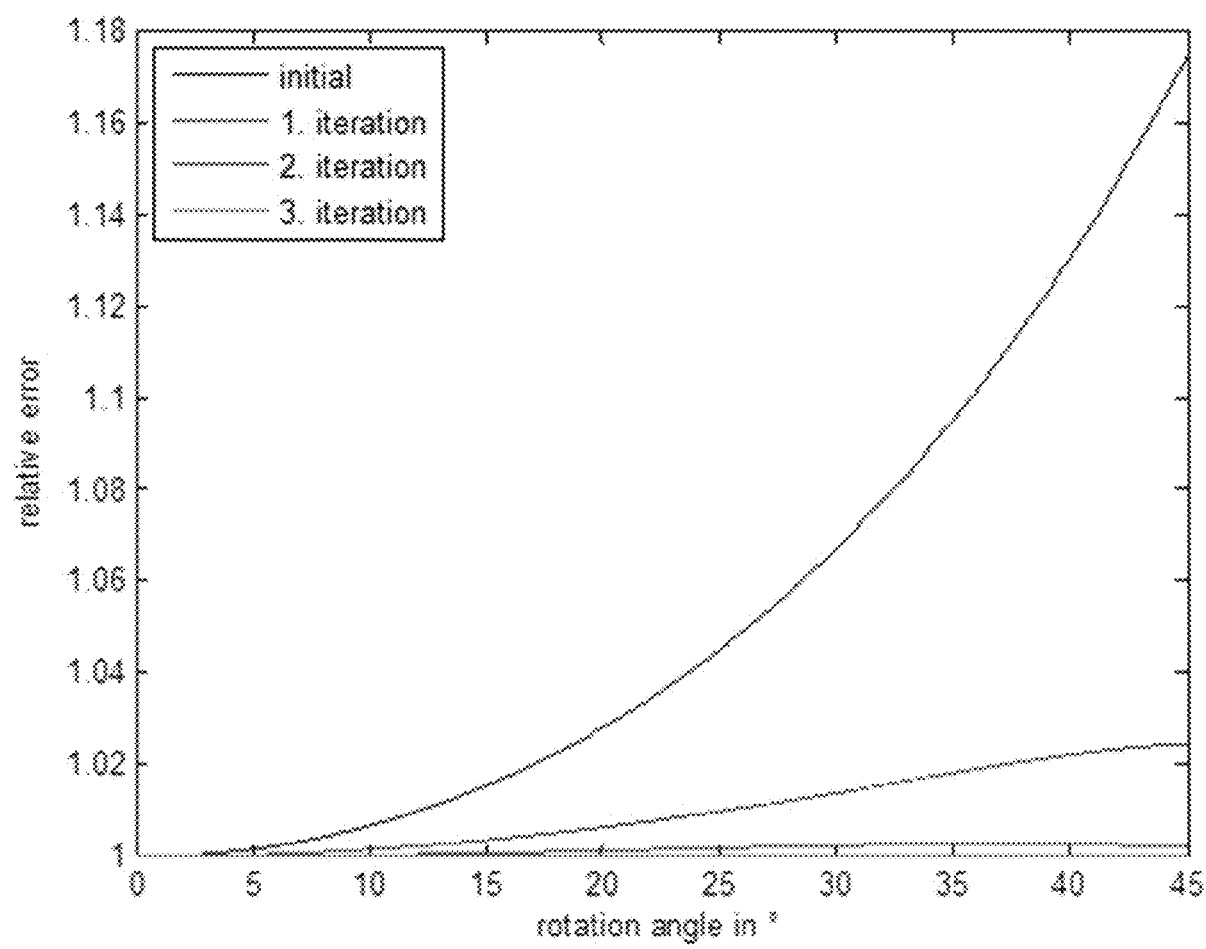
FIG. 6 shows a graph of relative error of the y-coordinate calculation for specific rotation angles over three iterations.

(with $x_{1m}>0$). For example, given some rotation angle $\alpha=20°$ and y=2: $x_{1m}=2.1759$ $x_{2m}=3.8841$ as shown in FIG. 4. Then start with an initial y=2.0557. A first iteration gives $\alpha=15.48°$ and y=2.0122. Then a second iteration improves that giving $\alpha=19.03°$ and y=2.0019, and a third iteration gets closer yet, with $\alpha=19.77°$ and y=1.9998. FIG. 6 shows a graph of the resulting relative error of the y-coordinate calculation for specific rotation angles, where the upper line is the initial estimate, the next line down is the improved relative error after one iteration of the algorithm, the next line down just above the x-axis shows even further reduction in relative error after two iterations, and after three iterations, the relative error is effectively zero (i.e., the x-axis).

The algorithm can be modified for only one iteration by multiplying a factor f to the estimation of $\widehat{x_3}$:

$$\widehat{x_3}' = f\widehat{x_3}$$

Figure 7:
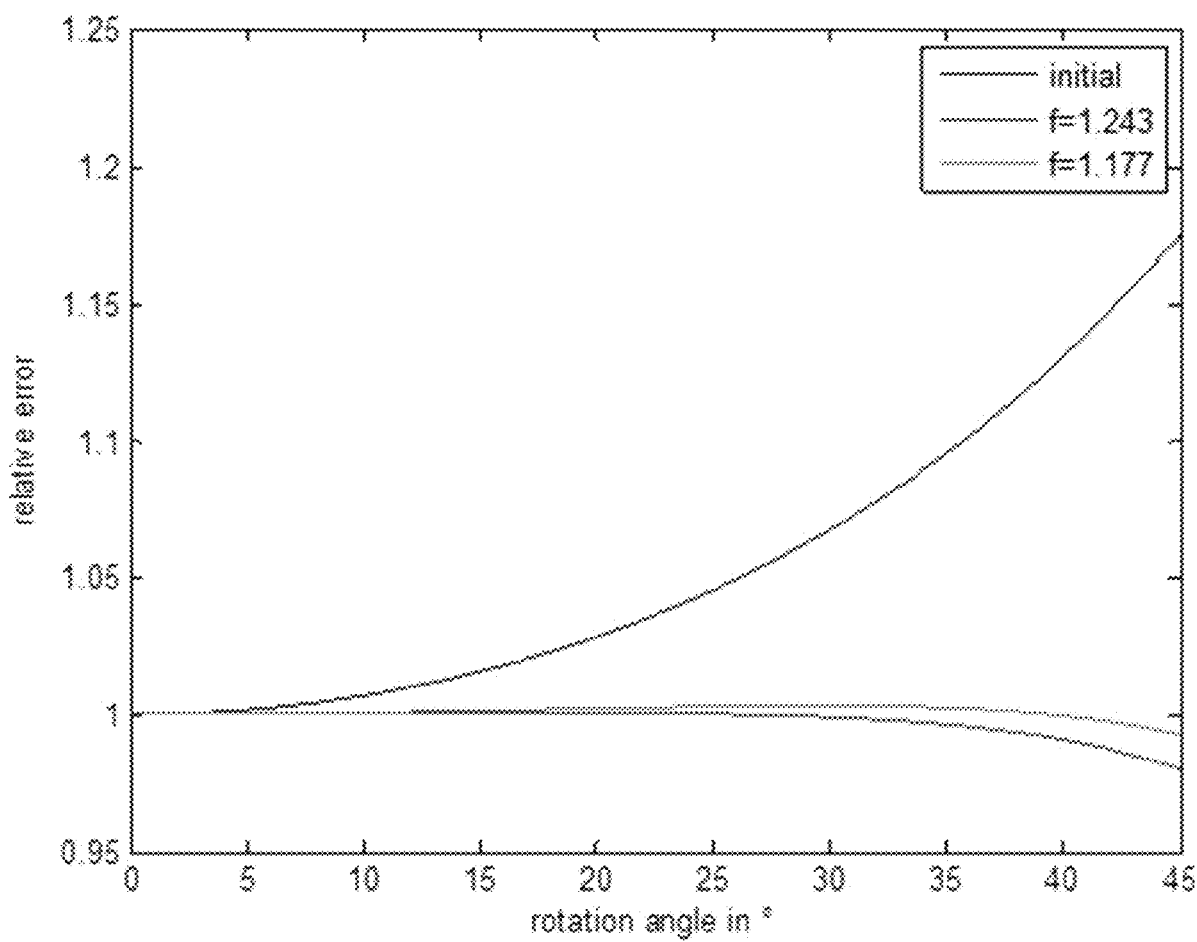
FIG. 7 shows a graph of relative error of the y-coordinate calculation for specific rotation angles for a single step non-iterative process with different weighting factors.

FIG. 7 shows a graph of the relative error of the y-coordinate calculation using such a single iteration weighting factor. Again the top line in FIG. 7 shows the relative error for the initial estimate, and the lower two lines show the data for a minimum error in the interval [0°, 45°] where f=1.177, and for a minimum error in the interval [0°, 30°] where f=1.243. This specific single iteration algorithm cannot later be used for further iterations.

Figure 5B:
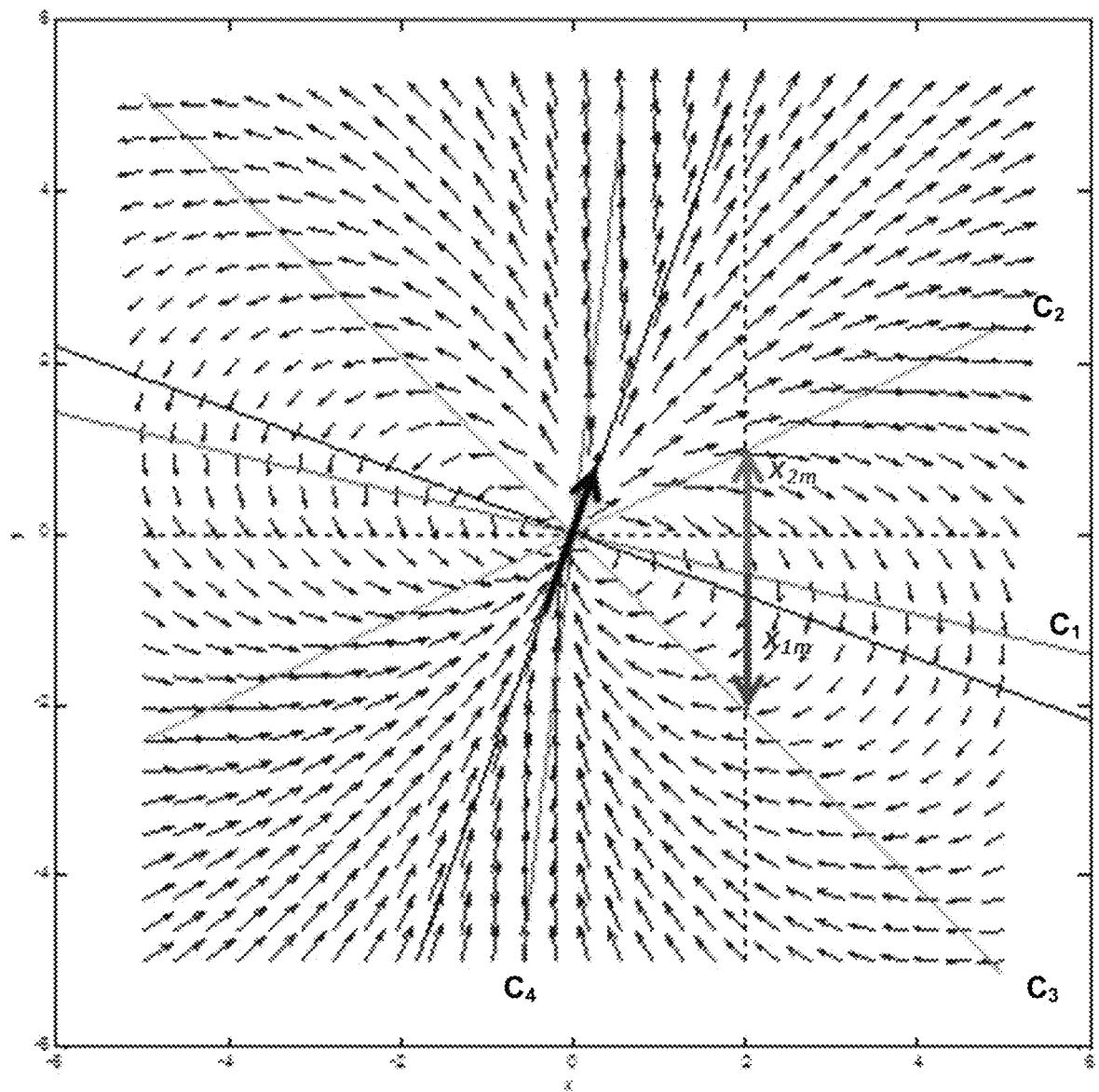

The described method works in a similar manner when the magnetic dipole of the implanted magnet is parallel to the skin of the patient. In that situation, a similar specific efficient algorithm may be used for finding the skin thickness in terms of the x-coordinate, the distance $x_{1m}$ is from upper point $B_x=0$ to point $B_y=0$, and the distance $x_{2m}$ is from lower point $B_x=0$ to point $B_y=0$, as shown in FIG. 5B. Then calculate a first estimate for distance y:

$$\hat{y} = \sqrt{2|x_{1m}x_{2m}|}$$

Calculate an estimate for rotation angle:

$$\hat{\alpha} = -\arctan\left(\frac{\hat{y}^2 - 2x_{2m}^2}{3\hat{y}x_{2m}}\right)$$

Then calculate an estimate for displacement of point $B_y=0$ to x=0

$$\widehat{x_3} = \frac{-3 + \sqrt{9 + 8(\tan \hat{\alpha})^2}}{2 \tan \hat{\alpha}} \hat{y}$$

And then update the measured distances:

$$x_1 = x_{1m} - \widehat{x_3}$$

$$x_2 = x_{2m} + \widehat{x_3}$$

from which:

$$\hat{y}' = \sqrt{2|x_1 x_2|}$$

Here ŷ' represents a better estimate for the unknown distance y. The algorithm can be further iterated to reduce the result error. Similarly it is possible to combine the first three calculations into a single step and to modify for only one iteration by multiplying a factor f to the estimation of $\widehat{y_3}$. Again, this specific single iteration algorithm cannot later be used for further iterations.

Specific embodiments may include a further step to identify the orientation of the magnet dipole in relation to the skin of the patient. For example, this identification can be determined by the orientation of the magnetic field at the left/upper or right/lower positions. The distances $x_{1m}$ and $x_{2m}$ represent the distances on the magnetic sensing array between the positions where the magnetic field components in x-direction and y-direction or y-direction and x-direction vanish. In the case where $B_x=0$ at the left/upper and right/lower point, the magnet dipole orientation is perpendicular to the patient skin and the efficient algorithm for this configuration is used to calculate the distance y. In the case where $B_y=0$ at the left/upper and right/lower point, the magnet dipole orientation is parallel to the patient skin and the efficient algorithm for this configuration is used to calculate the distance y.

The algorithm may be further modified by replacing the iterative step and angle calculation by a polynomial approximation and subsequent inverse mapping. In FIGS. 5A and 5B the field evaluation lines labelled from $c_1$ to $c_4$ are shown, where either the x- or the y-component of the magnetic field component vanishes. The lines go through the zero point and can be expressed by:

$$c_1(\alpha, x) = -\frac{-3 + \sqrt{9 + 8(\tan \alpha)^2}}{2 \tan \alpha} x = a_1(\alpha)x$$

$$c_4(\alpha, x) = -\frac{-3 + \sqrt{9 + 8(\tan \alpha)^2}}{2 \tan \alpha} x = a_4(\alpha)x$$

for the x-component of the magnetic field being zero ($B_x=0$), and expressed by:

$$c_2(\alpha, x) = \left(-\frac{3}{4}\tan \alpha + \frac{1}{4}\sqrt{9(\tan \alpha)^2 + 8}\right)x = a_2(\alpha)x$$

$$c_3(\alpha, x) = \left(-\frac{3}{4}\tan \alpha - \frac{1}{4}\sqrt{9(\tan \alpha)^2 + 8}\right)x = a_3(\alpha)x$$

for $B_y=0$. Each line equation $c_1$ to $c_4$ consists of a function of the angle $\alpha$ solely and denoted by $a_1(\alpha)$ to $a_4(\alpha)$ and x. Building the ratio of $x_{1m}$ and $x_{2m}$ cancels x out and is a function of the angle $\alpha$ only. For the case of the orientation of the magnetic dipole perpendicular to the skin of the patient yields:

$$z = \frac{x_{1m}}{x_{2m}}$$
$$= \frac{c_3(\alpha, x) - c_1(\alpha, x)}{c_2(\alpha, x) - c_{31}(\alpha, x)}$$
$$= \frac{a_3(\alpha) - a_1(\alpha)}{a_2(\alpha) - a_1(\alpha)}$$
$$= f(\alpha)$$

Figure 8A:
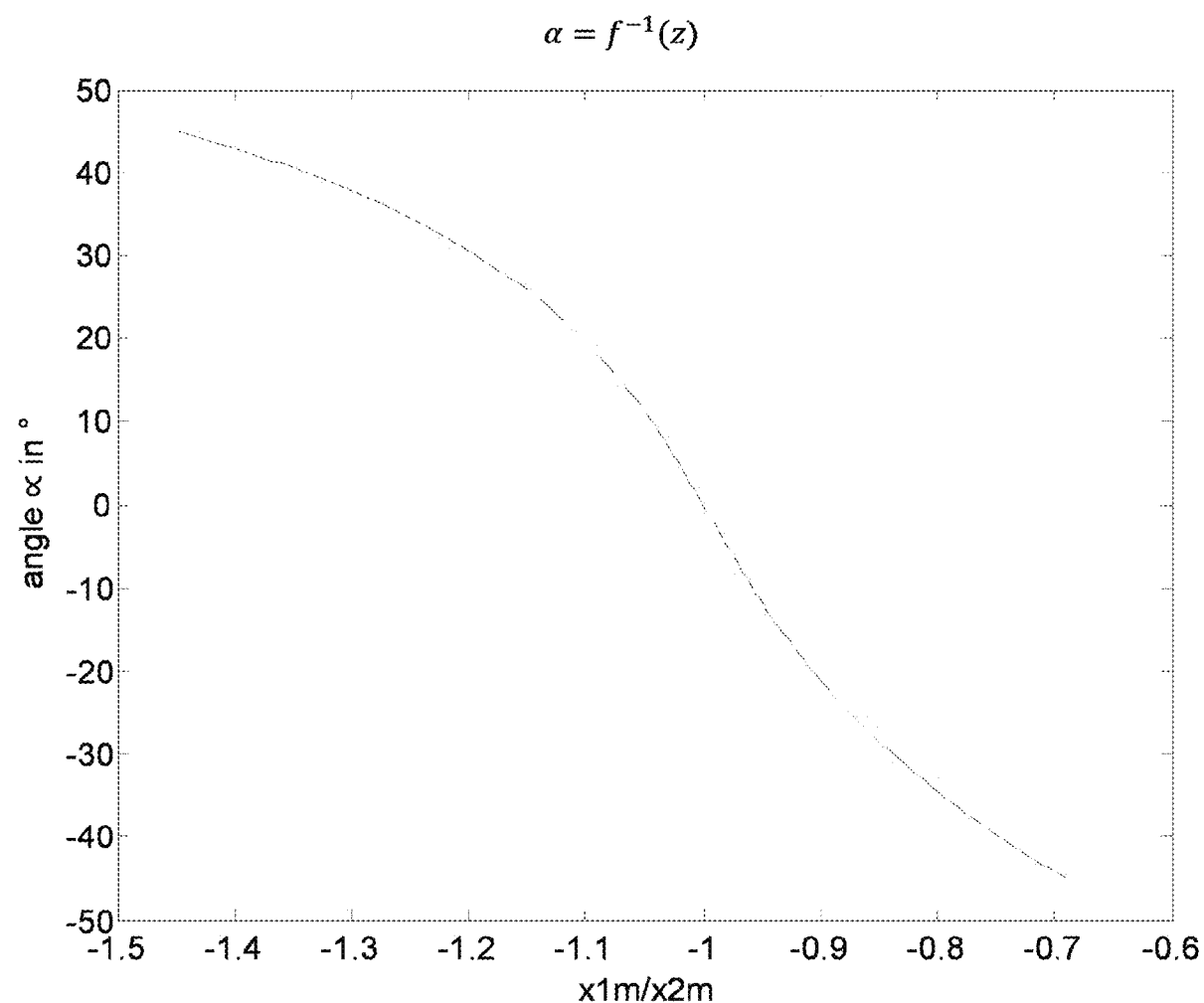
FIG. 8 A-B shows the inverse functions f and g for derivation of the angle $\propto$ from the ratio of the distances $x_{1m}$ and $x_{2m}$.

This function is invertible and the inverse function can be used to calculate the angle $\hat{\alpha}=f^{-1}(z)$. The inverse function, shown in FIG. 8A may be approximated by a polynomial. In one embodiment the polynomial may be of $8^{th}$ order. From this, the distance can be calculated by:

$$\hat{y} = \frac{x_{1m}}{\alpha_3(\hat{\alpha}) - a_1(\hat{\alpha})}$$

or alternatively by:

$$\hat{y} = \frac{x_{2m}}{\alpha_2(\hat{\alpha}) - a_1(\hat{\alpha})}$$

Both these functions may be approximated by a polynomial or any other interpolation technique known. For example piecewise linear interpolation or spline interpolation may be used. For the example shown in FIG. 4, given some rotation angle $\alpha<=20°$ and y=2: $x_{1m}$=2.1759 $x_{2m}$=3.8841, yields for $z=x_{1m}/x_{2m}$ and for $\alpha$=20.58°. Inserting the angle and calculating the distance yields y=1.9933.

In a similar manner the calculation for orientation of the magnetic dipole parallel to the patient skin is the distance calculated by:

$$\hat{y} = \frac{x_{1m}}{\frac{1}{\alpha_3(\hat{\alpha})} - \frac{1}{\alpha_4(\hat{\alpha})}}$$

or by:

$$\hat{y} = \frac{x_{2m}}{\frac{1}{\alpha_2(\hat{\alpha})} - \frac{1}{\alpha_4(\hat{\alpha})}}$$

Figure 8B:
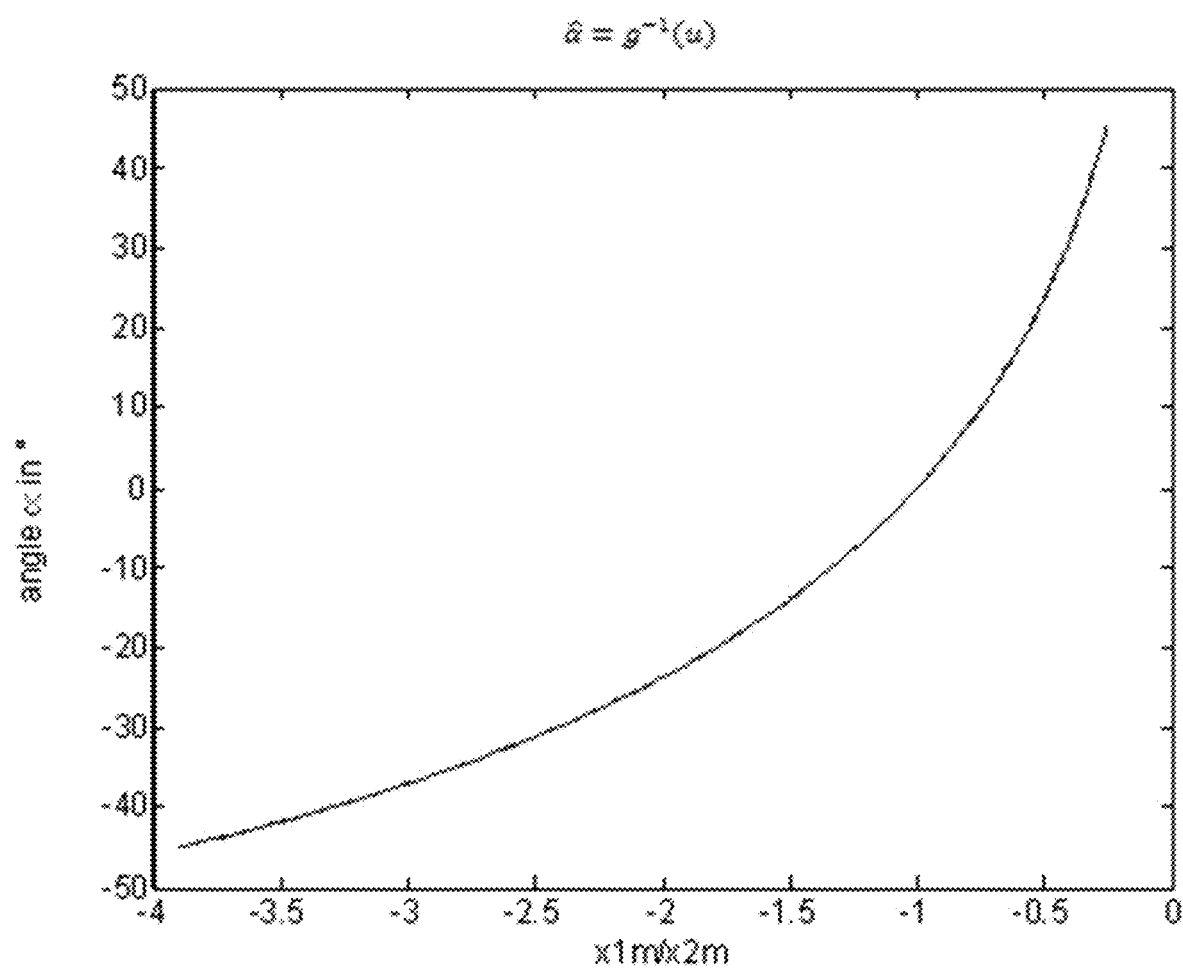

Both these functions may be approximated by a polynomial or any other interpolation technique known. For example piecewise linear interpolation or spline interpolation may be used. And the ratio of $x_{1m}$ and $x_{2m}$ is again a function of the angle $\alpha$ given by:

$$u = \frac{x_{1m}}{x_{2m}} = \frac{\frac{1}{a_3(\alpha)} - \frac{1}{a_4(\alpha)}}{\frac{1}{a_2(\alpha)} - \frac{1}{a_4(\alpha)}} = g(\alpha)$$

where this function is again invertible and he inverse function, shown in FIG. 8B, can be used to calculate the angle $\hat{\alpha}=g^{-1}(u)$. The inverse function may be approximated by a polynomial. In one embodiment the polynomial may be of $8^{th}$ order.

Figure 9A:
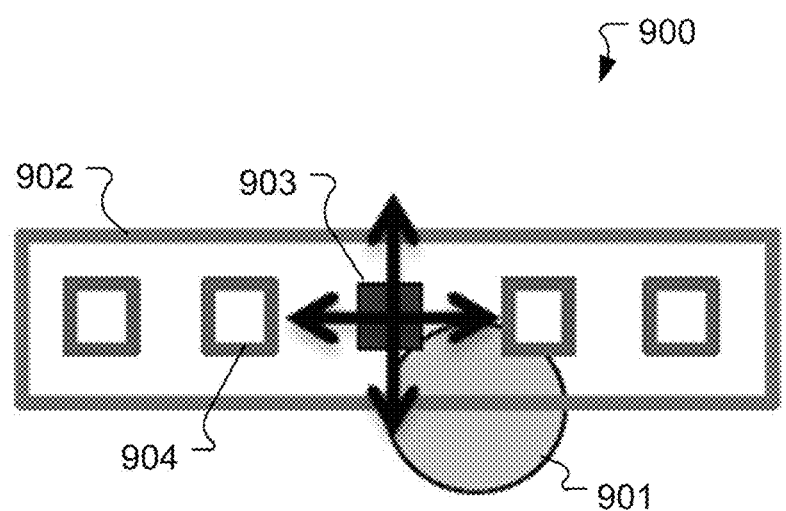
FIG. 9 A-B shows aligning with user interaction a one-dimensional sensor array for making magnetic field measurements.
Figure 9B:
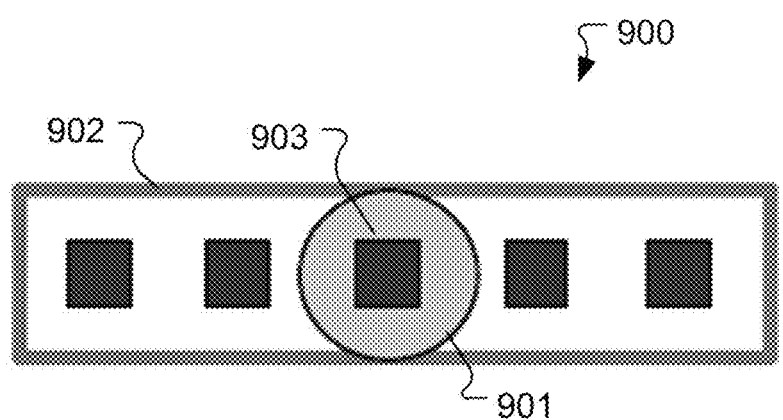

A one dimensional array 900 of magnetic sensors as shown in FIG. 9 A-B can be used to make the magnetic field measurements. The field evaluation lines need to be aligned so that the zero position of the measurement is in the middle of the position of the implant magnet 901. As shown in FIG. 9A, this zero position can be found by user interaction of the magnetic array 902 on the skin over the implant magnet 901 with just a single active sensor 903 in the center and the inactive sensors 904 elsewhere. The user moves the array 902 in two dimensions at the zero position in the measurement plane. The field strength can be visually indicated to the user, for example, using a bar plot, and the user then moves the array 902 to the position of maximum field strength (indicating that the array is aligned), and measurement with all the sensors and the complete array can then be performed, as shown in FIG. 9B.

Figure 10A:
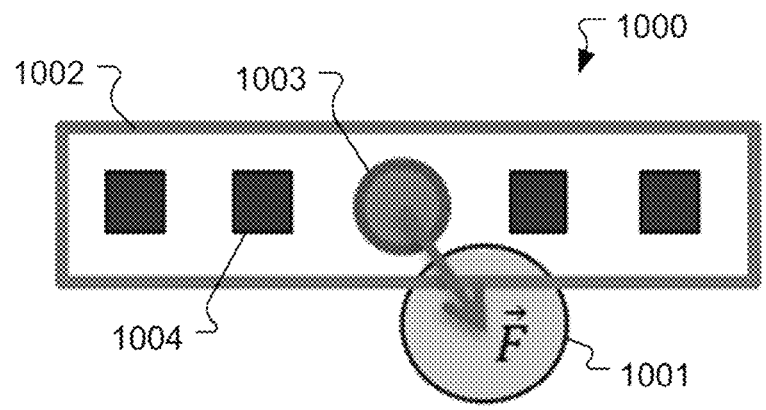
FIG. 10 A-C show aligning without user interaction a one-dimensional sensor array for making magnetic field measurements.
Figure 10B:
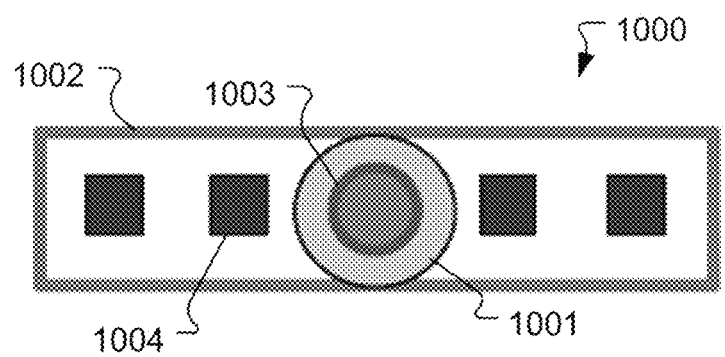
Figure 10C:
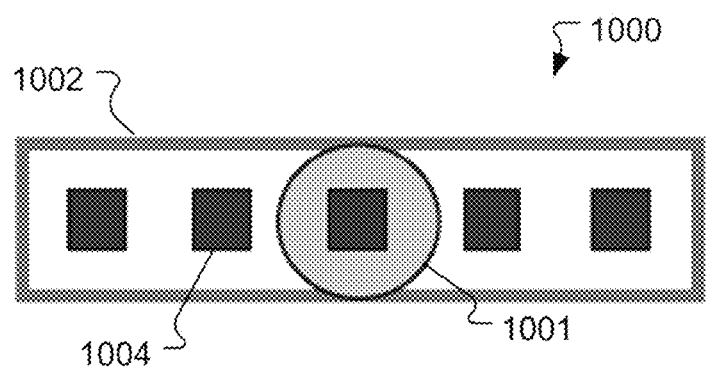

Rather than relying on user interaction to align the magnetic sensor array, some embodiments of a one dimensional sensor array can be aligned using an additional external magnet as shown in FIG. 10 A-C. FIG. 10A shows a one dimensional sensor array 1000 with an external magnet 1003 in the center of a magnetic array 1002 of multiple magnetic sensors 1004. The force of the magnetic interaction between the implant magnet 1001 and the external magnet 1003 moves the sensor array 1000 into the correct measurement position as shown in FIG. 10 A-B. In some embodiments, the effects of the external magnet 1003 may be included in the measurement procedure, or else the external magnet 1003 may be removed after the sensor array 1000 has been correctly positioned, as shown in FIG. 10C, and the field strength measurements then taken.

Figure 11A:
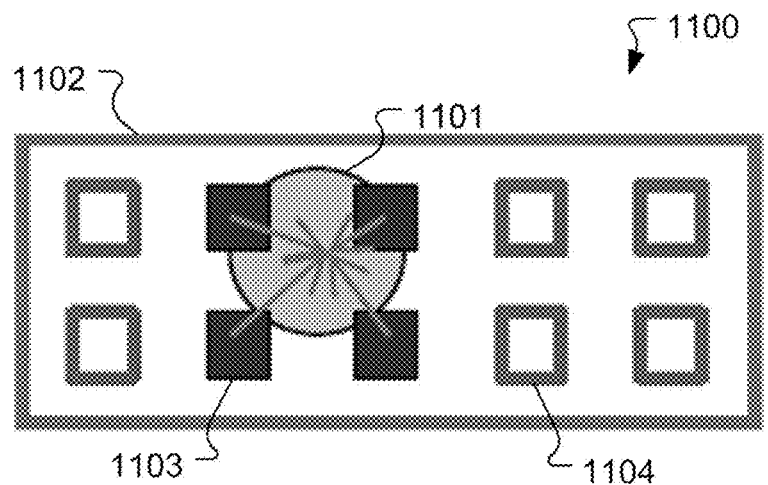
FIG. 11 A-B show using a two-dimensional sensor array for making magnetic field measurements.
Figure 11B:
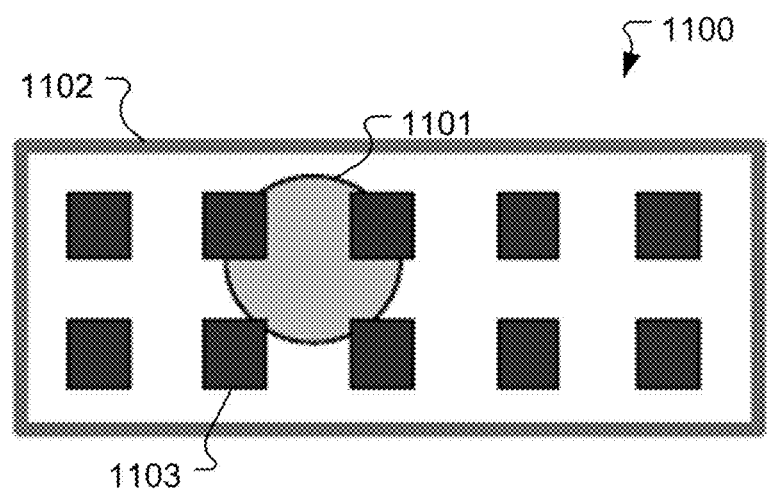

Instead of a one dimensional sensor array, some embodiments may use a two dimensional array to make the field strength measurements without user interaction. FIG. 11 A-B shows an embodiment of a two dimensional sensor array 1100 that includes a magnetic array 1102 having two rows of magnetic sensors. Initially the sensor array 1100 is placed on the skin approximately over the implant magnet 1101. The closest active sensors 1103 can be used to initially measure the magnetic field while the remain inactive sensors 1104 initially remain off, FIG. 11 A. The zero position can be calculated by estimation or interpolation of the field maximum from the measurements of the active sensors 1103. Once the offset position has been determined, the field measurements can be taken with all of the sensors active, FIG. 11B.

The foregoing approaches offer a distance estimation that corresponds to thickness of the skin over the implanted magnet which is numerically stable and can be efficiently computed. This is accomplished by purely passive measurement without the need to measure the orientation of the magnetic field. Rather it is sufficient to measure the magnetic field in one direction and find those points on the magnetic sensing array where in that direction the magnetic field component vanishes. This position on the magnetic measurement array can then be used to apply the algorithm to easily calculate the distance to the implant magnet.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of estimating a thickness of skin over an implanted magnet comprising:
    defining a plane perpendicular to the skin of a patient over the implanted magnet, characterized by x-axis and y-axis coordinates;
    aligning a measurement sensing array of magnetic sensors to a zero position which indicates a maximum magnetic field strength of the implanted magnet; and
    providing a computer processor configured to perform the steps of:
        1. measuring magnetic field strength of the implanted magnet using the aligned measurement sensing array of magnetic sensors on the skin of the patient;
        2. determining from the measured magnetic field strength at least one x-axis coordinate in the plane for at least one y-axis zero position on the array where a y-axis component of the measured magnetic field strength is zero; and
        3. calculating a y-axis coordinate of the at least one y-axis zero position using (i) the at least one x-axis coordinate and (ii) magnetic dipole moment of the implanted magnet, wherein the y-axis coordinate corresponds to the thickness of the skin over the implanted magnet.

2. The method according to claim 1, wherein x-axis co-ordinates are determined for two y-axis zero positions.

3. The method according to claim 1, wherein the magnetic field strength is measured using a one dimensional sensor array.

4. The method according to claim 1, wherein aligning the measurement sensing array comprises:
    visually indicating the magnetic field strength of the implanted magnet; and
    moving, by user-interaction, the measurement sensing array to the zero position.

5. The method according to claim 1, wherein the magnetic field strength is measured using a two dimensional sensor array.

6. The method according to claim 1, wherein calculating the y-axis coordinate is further a function of magnetic dipole moment rotation angle.

7. The method according to claim 1, wherein calculating the y-axis coordinate is based on an iterative calculation process.

8. The method according to claim 1, wherein calculating the y-axis coordinate is based on a trigonometric calculation process.

9. The method according to claim 1, wherein calculating the y-axis coordinate is based on single step non-iterative calculation process.

10. The method according to claim 9, wherein calculating the y-axis coordinate is based on calculating an inverse mapping.

11. The method according to claim 10, wherein calculating the inverse mapping is based on a polynomial function.

12. The method according to claim 11, wherein the polynomial function is based on the ratio of at least two x-axis coordinates.

13. The method according to claim 1, wherein aligning the measurement sensing array comprises:
    positioning an external magnet at the center of the measurement sensing array; and in response to a force of magnetic interaction between the implanted magnet and the external magnet, moving the measurement sensing array to the zero position.

14. A system for estimating a thickness of skin over a magnet implanted under the skin of a patient, the system comprising:

a measurement sensing array of magnetic sensors configured to measure magnetic field strength of the magnet, the measurement sensing array configured to be aligned to a zero position which indicates a maximum magnetic field strength of the magnet; and a processor coupled to the measurement sensing array and configured to:
   a. use the aligned measurement sensing array on the skin of the patient to measure the magnetic field strength of the magnet;
   b. for a plane perpendicular to the skin of the patient over the magnet characterized by x-axis and y-axis coordinates, determine from the measured magnetic field strength at least one x-axis coordinate in the plane for at least one y-axis zero position on the array where a y-axis component of the measured magnetic field strength is zero; and
   c. calculate a y-axis coordinate of the at least one y-axis zero position using (i) the at least one x-axis coordinate and (ii) magnetic dipole moment of the implanted magnet, wherein the y-axis coordinate corresponds to the thickness of the skin over the implanted magnet.

* * * * *

UNITED STATES PATENT AND TRADEMARK OFFICE
CERTIFICATE OF CORRECTION

PATENT NO. : 11,369,283 B2
APPLICATION NO. : 14/522677
DATED : June 28, 2022
INVENTOR(S) : Christoph Hornsteiner It is certified that error appears in the above-identified patent and that said Letters Patent is hereby corrected as shown below:

In the Claims

In Column 10, Line 31:
Claim 2, replace "co-ordinates" with --coordinates--

Signed and Sealed this
First Day of November, 2022

Katherine Kelly Vidal
*Director of the United States Patent and Trademark Office*